US012784568B2

(12) United States Patent
Shen et al.

(10) Patent No.: US 12,784,568 B2
(45) Date of Patent: Nov. 3, 2026

(54) DRIVER MONITORING SYSTEM AND DRIVER MONITORING METHOD

(71) Applicant: Hon Hai Precision Industry Co., Ltd., New Taipei City (TW)

(72) Inventors: San Sheng Shen, New Taipei City (TW); Chin Hui Lin, New Taipei City (TW)

(73) Assignee: Hon Hai Precision Industry Co., Ltd., New Taipei City (TW)

(*) Notice: Subject to any disclaimer, the term of this patent is extended or adjusted under 35 U.S.C. 154(b) by 9 days.

(21) Appl. No.: 19/047,657

(22) Filed: Feb. 7, 2025

(65) Prior Publication Data

US 2026/0112260 A1 Apr. 23, 2026

(30) Foreign Application Priority Data

Oct. 17, 2024 (TW) ................................. 113139471

(51) Int. Cl.

| | |
|---|---|
| ***G08B 21/06*** | (2006.01) |
| ***A61B 5/00*** | (2006.01) |
| ***A61B 5/024*** | (2006.01) |
| ***A61B 5/05*** | (2021.01) |
| ***A61B 5/16*** | (2006.01) |
| ***A61B 5/18*** | (2006.01) |
| ***B60Q 9/00*** | (2006.01) |

(52) U.S. Cl.

CPC .......... *G08B 21/06* (2013.01); *A61B 5/02405* (2013.01); *A61B 5/05* (2013.01); *A61B 5/165* (2013.01); *A61B 5/18* (2013.01); *A61B 5/6893* (2013.01); *A61B 5/7257* (2013.01); *A61B 5/746* (2013.01); *B60Q 9/00* (2013.01); *A61B 2503/22* (2013.01)

(58) Field of Classification Search

None

See application file for complete search history.

(56) References Cited

U.S. PATENT DOCUMENTS

| | | | | |
|---|---|---|---|---|
| 8,725,311 | B1 * | 5/2014 | Breed ...................... | A61B 5/11 701/1 |
| 10,696,305 | B2 | 6/2020 | Zhang et al. | |

(Continued)

FOREIGN PATENT DOCUMENTS

| | | |
|---|---|---|
| CN | 111657889 | 9/2020 |
| CN | 114041794 | 2/2022 |

(Continued)

OTHER PUBLICATIONS

"Office Action of Taiwan Counterpart Application", issued on Aug. 21, 2025, p. 1-p. 6.

*Primary Examiner* — Fekadeselassie Girma

(74) *Attorney, Agent, or Firm* — JCIPRNET

(57) ABSTRACT

Provided are a driver monitoring system and a driver monitoring method. The driver monitoring method includes: detecting a first heartbeat signal of a driver through a radar; extracting a beat-to-beat interval signal from the first heartbeat signal; generating heart rate variability data according to the beat-to-beat interval signal, where the heart rate variability data includes low frequency power and high frequency power; determining whether the driver is fatigued according to the heart rate variability data; and in response to determining that the driver is fatigued, outputting an alarm message.

18 Claims, 4 Drawing Sheets

(56) References Cited

U.S. PATENT DOCUMENTS

| | | | | |
|---|---|---|---|---|
| 12,115,995 | B2 * | 10/2024 | Khamis | A61B 5/18 |
| 12,159,470 | B2 * | 12/2024 | Reiner | B60W 40/08 |
| 12,204,958 | B2 * | 1/2025 | Pitre | G06N 3/047 |
| 12,245,738 | B2 * | 3/2025 | Ozawa | A61B 5/02141 |
| 12,444,291 | B1 * | 10/2025 | Ross, Jr. | G05B 19/0428 |
| 12,459,355 | B2 * | 11/2025 | Nakamura | B60K 28/06 |
| 12,514,507 | B2 * | 1/2026 | Komine | A61B 5/18 |
| 2005/0073424 | A1 * | 4/2005 | Ruoss | A61B 5/18 342/61 |
| 2009/0227882 | A1 * | 9/2009 | Foo | A61B 5/7207 343/893 |
| 2014/0276090 | A1 * | 9/2014 | Breed | A61B 5/1455 600/473 |
| 2014/0371603 | A1 * | 12/2014 | Fujita | A61B 5/18 600/479 |
| 2017/0071546 | A1 * | 3/2017 | Jain | A61B 5/0533 |
| 2017/0112412 | A1 * | 4/2017 | Garbos | A61B 5/6898 |
| 2019/0332902 | A1 * | 10/2019 | Gallagher | G06V 10/811 |
| 2020/0335211 | A1 * | 10/2020 | Gopalakrishnan | A61B 5/002 |
| 2021/0016805 | A1 * | 1/2021 | Oba | B60W 40/08 |
| 2021/0197832 | A1 * | 7/2021 | Matsunami | A61B 5/02055 |
| 2023/0080306 | A1 * | 3/2023 | Cho | B60W 50/14 701/36 |
| 2023/0190100 | A1 * | 6/2023 | Stump | A61B 5/746 600/301 |
| 2024/0335140 | A1 * | 10/2024 | Tedgue Beltrao | A61B 5/0507 |
| 2025/0054601 | A1 * | 2/2025 | Carr | A61B 5/4809 |
| 2025/0263013 | A1 * | 8/2025 | Kimani | A61B 5/0002 |
| 2025/0380108 | A1 * | 12/2025 | Judge | H04W 4/021 |
| 2026/0018039 | A1 * | 1/2026 | Deixler | G08B 21/043 |

FOREIGN PATENT DOCUMENTS

| | | | | | |
|---|---|---|---|---|---|
| EP | 2020919 | B1 * | 7/2019 | | A61B 5/4818 |
| WO | WO-2020080569 | A1 * | 4/2020 | | B60K 28/06 |

* cited by examiner

DRIVER MONITORING SYSTEM AND DRIVER MONITORING METHOD

CROSS-REFERENCE TO RELATED APPLICATION

This application claims the priority benefit of Taiwan application serial no. 113139471, filed on Oct. 17, 2024. The entirety of the above-mentioned patent application is hereby incorporated by reference herein and made a part of this specification.

BACKGROUND

Technical Field

This disclosure relates to a monitoring technology, and in particular to a driver monitoring system and a driver monitoring method.

Description of Related Art

Conventional driver monitoring systems (DMS) use cameras to monitor the interior of the vehicle and determine the physiological state or fatigue level of the driver based on the images captured by the cameras. However, DMS based on image recognition technology is prone to misjudging the state of the driver. For example, eyes of a driver may be too small for the DMS to misjudge that the driver has gone to sleep. In addition, the use of images to monitor driving may violate the privacy of the driver or passengers. Therefore, how to provide a driver monitoring system that can overcome the above disadvantages is one of the important issues in this field.

SUMMARY

The disclosure provides a driver monitoring system and a driver monitoring method, capable of monitoring a physiological state of a driver to determine whether the driver is fatigued.

The driver monitoring system of the disclosure includes a radar and a processor. The processor is coupled to the radar, where the processor is configured to perform: detect a first heartbeat signal of a driver through the radar; extract a beat-to-beat interval signal from the first heartbeat signal; generate heart rate variability data according to the beat-to-beat interval signal, where the heart rate variability data includes low frequency power and high frequency power; determine whether the driver is fatigued according to the heart rate variability data; and in response to determining that the driver is fatigued, output an alarm message.

In an embodiment of the disclosure, the processor is configured to further: obtain a historical data set, where the historical data set includes historical heart rate variability data, where the historical heart rate variability data includes historical low frequency power and historical high frequency power; calculate a P-value of the heart rate variability data according to the historical data set and the heart rate variability data; and determine whether the driver is fatigued according to the P-value.

In an embodiment of the disclosure, the processor is configured to further: in response to the P-value being less than a threshold, determine that the driver is fatigued.

In an embodiment of the disclosure, the processor calculates the P-value according to one of the following: analysis of variance, T-test, or F-test.

In an embodiment of the disclosure, the processor is configured to further: add the heart rate variability data to the historical data set to update the historical data set.

In an embodiment of the disclosure, the processor is configured to further: detect the first heartbeat signal and a second heartbeat signal of the driver according to a preset period, where the second heartbeat signal is later than the first heartbeat signal; and determine whether the driver is fatigued according to the updated historical data set and the second heartbeat signal.

In an embodiment of the disclosure, the heart rate variability data further includes a standard deviation of the beat-to-beat interval signal and a ratio of the low frequency power to the high frequency power.

In an embodiment of the disclosure, the beat-to-beat interval signal includes a first beat-to-beat interval, and where the processor is configured to further: detect a first wave peak and a second wave peak of the first heartbeat signal, where the first wave peak and the second wave peak are adjacent wave peaks; and calculate a time interval between the first wave peak and the second wave peak to obtain the first beat-to-beat interval.

In an embodiment of the disclosure, the processor is configured to further: perform a discrete Fourier transform on the beat-to-beat interval signal to obtain a frequency response; and obtain the low frequency power and the high frequency power from the frequency response.

In an embodiment of the disclosure, the processor is configured to further: detect a field in a vehicle through the radar to determine whether the driver exists; and in response to determining that the driver exists, detect the first heartbeat signal of the driver through the radar.

The driver monitoring method of the disclosure includes the following. A first heartbeat signal of a driver is detected through a radar. A beat-to-beat interval signal is extracted from the first heartbeat signal. Heart rate variability data according to the beat-to-beat interval signal is generated, where the heart rate variability data includes low frequency power and high frequency power. Whether the driver is fatigued is determined according to the heart rate variability data. In response to determining that the driver is fatigued, an alarm message is output.

In one embodiment of the disclosure, determining whether the driver is fatigued according to the heart rate variability data includes the following. A historical data set is obtained, where the historical data set includes historical heart rate variability data, where the historical heart rate variability data includes historical low frequency power and historical high frequency power. A P-value of the heart rate variability data is calculated according to the historical data set and the heart rate variability data. Whether the driver is fatigued is determined according to the P-value.

In an embodiment of the disclosure, determining whether the driver is fatigued according to the P-value includes the following. In response to the P-value being less than a threshold, that the driver is fatigued is determined.

In an embodiment of the disclosure, the driver monitoring method further includes the following. The P-value is calculated according to one of the following: analysis of variance, T test, or F test.

In an embodiment of the disclosure, the driver monitoring method further includes the following. The heart rate variability data is added to the historical data set to update the historical data set.

In an embodiment of the disclosure, the driver monitoring method further includes the following. The first heartbeat signal and a second heartbeat signal of the driver are detected according to a preset period, where the second heartbeat signal is later than the first heartbeat signal. Whether the driver is fatigued is determined according to the updated historical data set and the second heartbeat signal.

In an embodiment of the disclosure, the heart rate variability data further includes a standard deviation of the beat-to-beat interval signal and a ratio of the low frequency power to the high frequency power.

In an embodiment of the disclosure, the beat-to-beat interval signal includes a first beat-to-beat interval, where extracting the beat-to-beat interval signal from the first heartbeat signal includes the following. A first wave peak and a second wave peak of the first heartbeat signal are detected, where the first wave peak and the second wave peak are adjacent wave peaks. A time interval between the first wave peak and the second wave peak is calculated to obtain the first beat-to-beat interval.

In an embodiment of the disclosure, generating the heart rate variability data according to the beat-to-beat interval signal includes the following. A discrete Fourier transform is performed on the beat-to-beat interval signal to obtain a frequency response. The low frequency power and the high frequency power are obtained from the frequency response.

In an embodiment of the disclosure, the driver monitoring method further includes the following. A field in a vehicle is detected through the radar to determine whether the driver exists. In response to determining that the driver exists, the first heartbeat signal of the driver is detected through the radar.

Based on the above, the driver monitoring system of the disclosure can detect the heartbeat signal of the driver through radar, and determine the sympathetic activity or parasympathetic activity of the driver according to the heartbeat signal, thereby determining whether the driver is fatigued.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate example embodiments of the disclosure and, together with the description, serve to explain the principles of the disclosure.

DESCRIPTION OF THE EMBODIMENTS

Figure 1:
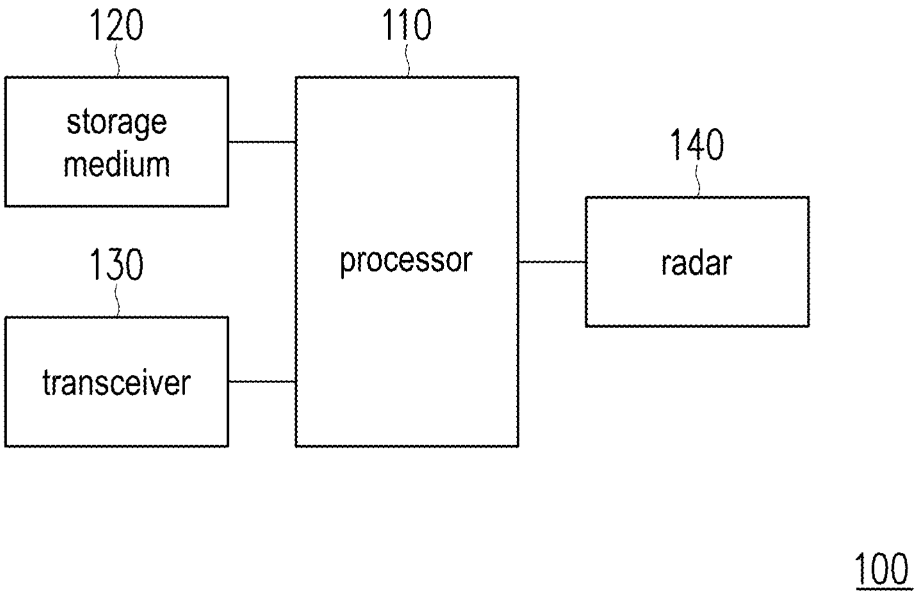
FIG. 1 illustrates a schematic diagram of a driver monitoring system according to an embodiment of the disclosure.

In order to make the content of the disclosure easier to understand, the following embodiments are provided as examples according to which the disclosure can be implemented. In addition, wherever possible, elements/components/steps with the same reference numerals in the drawings and embodiments represent the same or similar parts.

FIG. 1 illustrates a schematic diagram of a driver monitoring system 100 according to an embodiment of the disclosure. The driver monitoring system 100 may include a processor 110, a storage medium 120, a transceiver 130, and a radar 140.

The processor 110 is, for example, a central processing unit (CPU), or other programmable general-purpose or special-purpose micro control unit (MCU), microprocessor, digital signal processor (DSP), programmable controller, application specific integrated circuit (ASIC), graphics processing unit (GPU), image signal processor (ISP)), image processing unit (IPU), arithmetic logic unit (ALU), complex programmable logic device (CPLD), field programmable gate array (FPGA), or other similar components or a combination of the above components. The processor 110 can be coupled to the storage medium 120, the transceiver 130, and the radar 140, and access and execute multiple modules and various applications stored in the storage medium 120.

The storage medium 120 is, for example, any type of fixed or removable random access memory (RAM), read-only memory (ROM), or flash memory, hard disk drive (HDD), solid state drive (SSD), or similar components or a combination of the above components, used to store multiple modules or various applications that can be executed by the processor 110.

The transceiver 130 transmits or receives signals in a wireless or wired manner. The transceiver 130 may also perform operations such as low noise amplification, impedance matching, mixing, up or down frequency conversion, filtering, amplification, and similar operations.

The radar 140 can transmit radio frequency signals and receive reflected signals of radio frequency signals. The processor 110 may use the radar 140 to detect objects. The radar 140 may include, but is not limited to, millimeter wave (mmWave) radar or frequency modulated continuous wave (FMCW) radar.

Figure 2:
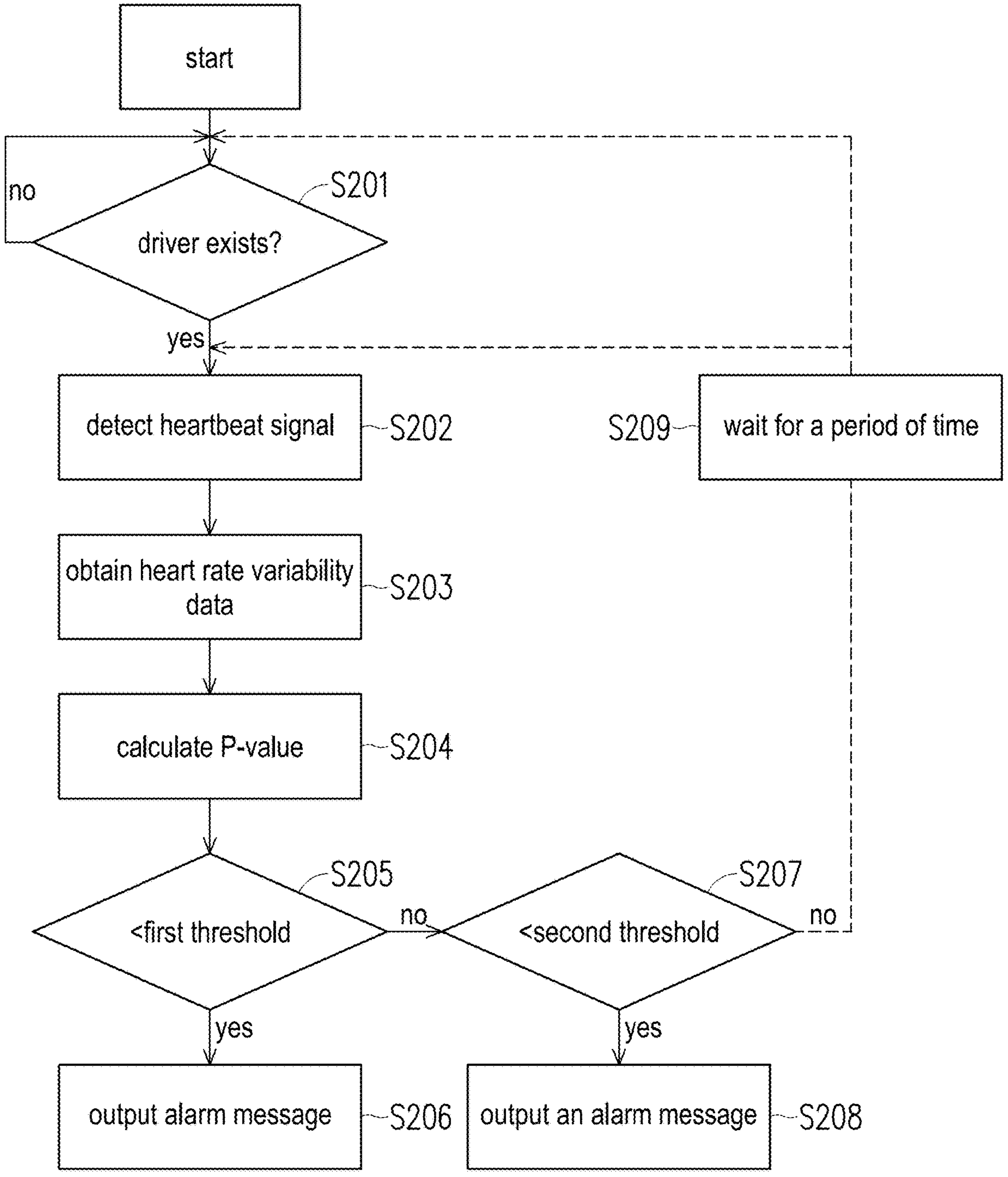
FIG. 2 illustrates a flow chart of a driver monitoring method according to an embodiment of the disclosure.

FIG. 2 illustrates a flow chart of a driver monitoring method according to an embodiment of the disclosure, where the driver monitoring method can be implemented by the driver monitoring system 100 shown in FIG. 1. In step S201, the processor 110 may detect the presence of a driver through the radar 140. For example, the processor 110 can transmit a radio frequency signal to a field in the carrier (such as a seat of the driver) through the radar 140 and receive a reflected signal of the radio frequency signal. The processor 110 may analyze the reflected signal to determine whether there is a driver in the field. If the processor 110 detects the presence of a driver, step S202 is entered. If the processor 110 does not detect the presence of a driver, the processor 110 may re-execute step S201 after waiting for a period of time. In an embodiment, the processor 110 may re-execute step S201 based on a preset period to detect whether a driver exists.

In step S202, the processor 110 may detect a heartbeat signal of the driver through the radar 140. For example, the processor 110 can detect the chest displacement of the driver through the radar 140, thereby obtaining the heartbeat signal of the driver.

In step S203, the processor 110 may extract a beat-to-beat interval signal from the heartbeat signal and generate heart rate variability (HRV) data according to the beat-to-beat interval. In one embodiment, the beat-to-beat interval signal is, for example, a RR interval signal.

Figure 3:
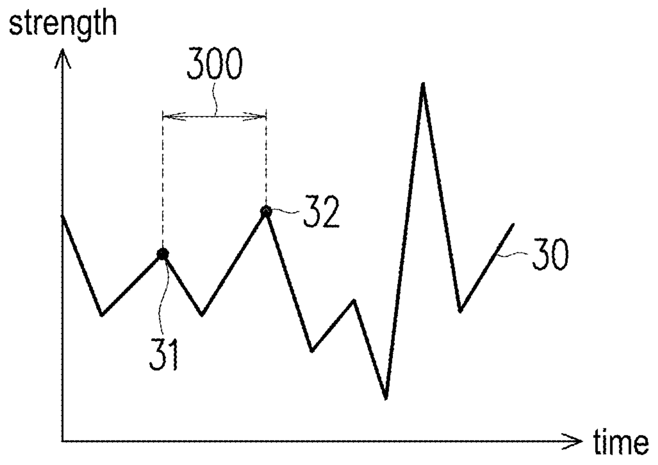
FIG. 3 illustrates a schematic diagram of a heartbeat signal according to an embodiment of the disclosure.

The beat-to-beat interval signal can contain one or more beat-to-beat intervals. Specifically, the processor 110 can detect two adjacent wave peaks in the heartbeat signal. Then, the processor 110 may calculate the time interval between the two adjacent wave peaks to obtain the beat-to-beat interval. For example, FIG. 3 illustrates a schematic diagram of a heartbeat signal 30 according to an embodiment of the disclosure. The processor 110 can detect a wave peak 31 and a wave peak 32 of the heartbeat signal 30, where the wave peak 31 and the wave peak 32 are adjacent wave peaks. Then, the processor 110 can calculate a time interval 300 between the wave peak 31 and the wave peak 32 to obtain the beat-to-beat interval. The processor 110 may obtain one or more beat-to-beat intervals from the heartbeat signal 30 to generate a beat-to-beat interval signal.

In one embodiment, the processor 110 may perform time domain analysis on the beat-to-beat interval signal to obtain one or more time domain HRV data. Time domain HRV data can include the standard deviation of NN intervals (SDNN) or the standard deviation of average NN intervals (SDANN) and other standard deviations data associated with the beat-to-beat interval signal.

In one embodiment, the processor 110 may perform a discrete Fourier transform (DFT) on the beat-to-beat interval signal to obtain a frequency response, and obtain one or more frequency domain HRV data according to the frequency response. The frequency domain HRV data can include total power (TP), very low frequency power (VLFP), low frequency power (LFP) representing sympathetic activity and parasympathetic activity, high frequency power (HFP) representing parasympathetic activity, normalized low frequency power (nLFP) representing a quantitative indicator of sympathetic activity, normalized high frequency power (nHFP) representing a quantitative indicator of parasympathetic activity, or a LF/HF ratio representing autonomic balance. LFP can contain power in the frequency band 0.04 Hz to 0.15 Hz. HFP can contain power in the frequency band 0.15 Hz to 0.4 Hz.

Figure 4:
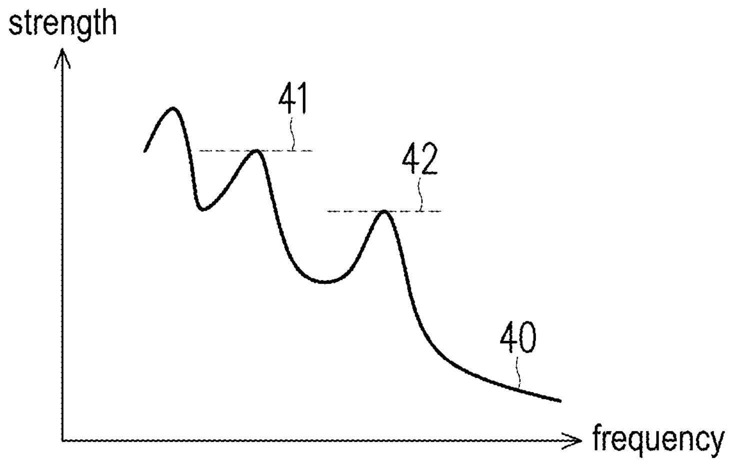
FIG. 4 is a schematic diagram of frequency response according to an embodiment of the disclosure.

For example, FIG. 4 is a schematic diagram of a frequency response 40 according to an embodiment of the disclosure. The processor 110 may perform DFT on the beat-to-beat interval signal to obtain the frequency response 40, where the frequency response 40 may include low frequency power 41 and high frequency power 42. The processor 110 may divide the low frequency power 41 by the high frequency power 42 to obtain the LF/HF ratio.

In one embodiment, before performing DFT on the beat-to-beat interval signal, the processor 110 may perform interpolation or resampling on the beat-to-beat interval signal.

Returning to FIG. 2, in step S204, the processor 110 may calculate a P-value of the HRV data. In one embodiment, the processor 110 may calculate the P-value of the HRV data according to analysis of variance (ANOVA), T-test, or F-test.

Specifically, before obtaining the HRV data and calculating the P-value of the HRV data, the processor 110 may receive a historical data set through the transceiver 130 or detect the driver through the radar 140 to obtain the historical data set. The historical data set may include multiple historical HRV data, and each historical HRV data may include data such as historical LFP or historical HFP. The processor 110 can determine whether the amount of historical HRV data in the historical data set is sufficient. If the amount of historical HRV data is less than or equal to a threshold, the processor 110 can continuously obtain new historical HRV data and add the new historical HRV data to the historical data set. If the amount of historical HRV data is greater than the threshold, the processor 110 can calculate the mean and standard deviation of the historical data set to obtain the distribution of the historical data set.

After obtaining the distribution of the historical data set, the processor 110 can calculate a T-value or a F-value of the HRV data according to the mean and standard deviation of the historical data set and the HRV data. Next, the processor 110 may calculate a cumulative distribution function (CDF) value according to the distribution of the historical data set and the value (i.e., T-value or F-value) of the HRV data to obtain the P-value of the HRV data.

In one embodiment, after obtaining the HRV data, the processor 110 may add the HRV data to the historical data set to update the historical data set. The updated historical data set can be used to calculate the P-value for new HRV data obtained by processor 110 in the future.

In step S205, the processor 110 may determine whether the P-value of the HRV data is less than a first threshold, where the first threshold is equal to 0.01, for example. If the P-value is less than the first threshold, proceed to step S206. In step S206, the processor 110 may determine that the driver is in a fatigued state, and that the fatigue level of the driver is severe. The processor 110 can output an alarm message to indicate that the fatigue level of the driver is severe. For example, the processor 110 can communicate with an output device such as a display device or a speaker through the transceiver 130, and output an alarm message through the output device. On the other hand, if the P-value is greater than or equal to the first threshold, then proceed to step S207.

In step S207, the processor 110 may determine whether the P-value of the HRV data is less than a second threshold, where the second threshold is greater than the first threshold. The second threshold is equal to 0.05, for example. If the P-value is less than the second threshold, proceed to step S208. In step S208, the processor 110 may determine that the driver is in a fatigued state. The processor 110 can output an alarm message to indicate that the driver is in a fatigued state. For example, the processor 110 can communicate with an output device such as a display device or a speaker through the transceiver 130, and output an alarm message through the output device.

On the other hand, if the P-value is greater than or equal to the second threshold, proceed to step S209. In step S209, the processor 110 may wait for a period of time based on a preset period. Then, the processor 110 can re-execute step S201 or step S202.

Figure 5:
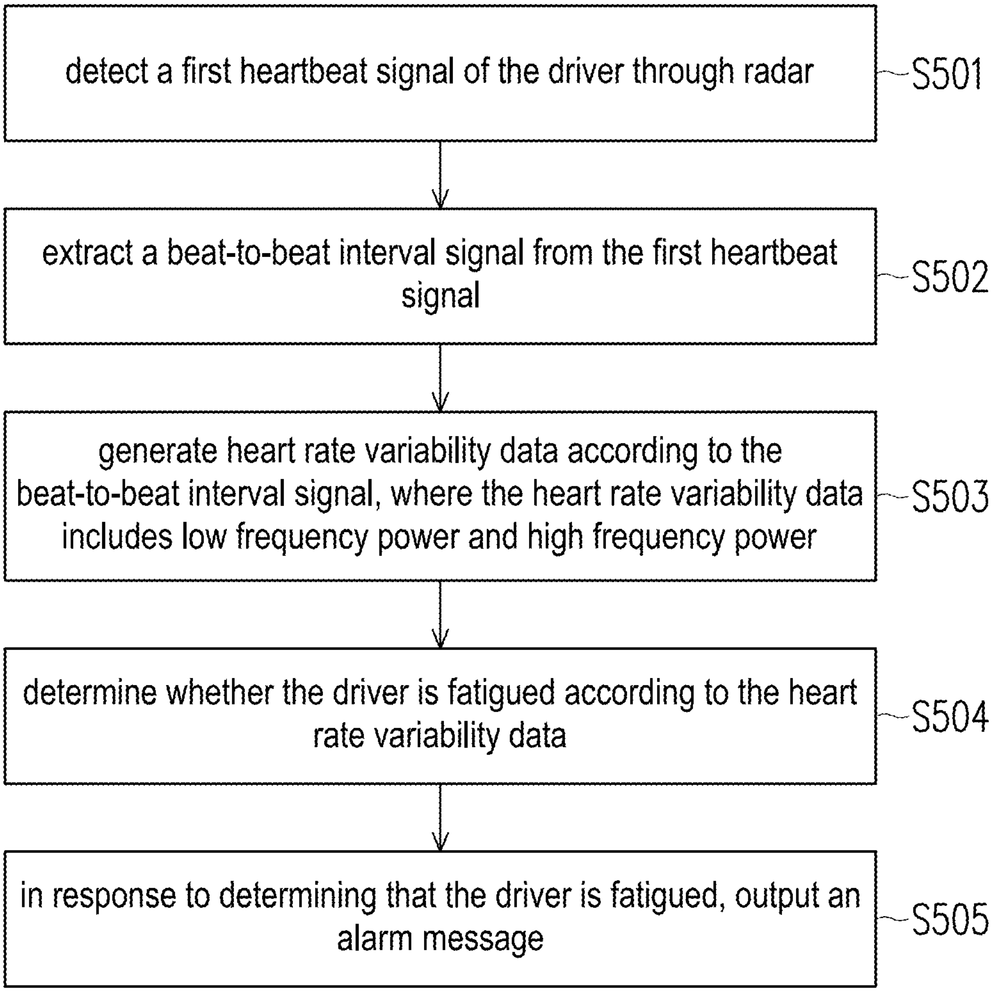
FIG. 5 illustrates a flow chart of a driver monitoring method according to an embodiment of the disclosure.

FIG. 5 illustrates a flow chart of a driver monitoring method according to an embodiment of the disclosure, where the driver monitoring method can be implemented by the driver monitoring system 100 shown in FIG. 1. In step S501, a first heartbeat signal of the driver is detected through radar. In step S502, a beat-to-beat interval signal is extracted from the first heartbeat signal. In step S503, heart rate variability data is generated according to the beat-to-beat interval signal, where the heart rate variability data includes low frequency power and high frequency power. In step S504, whether the driver is fatigued is determined according to the heart rate variability data. In step S505, in response to determining that the driver is fatigued, an alarm message is output.

To sum up, the driver monitoring system of the disclosure can detect the heartbeat signal of the driver through radar, and determine the sympathetic activity or parasympathetic activity of the driver according to the heartbeat signal, thereby determining whether the driver is fatigued. Compared to the conventional driver monitoring system using image recognition technology, the driver monitoring system of the disclosure has higher accuracy and protects the privacy of the driver and passengers.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A driver monitoring system, comprising:

a radar; and a processor, coupled to the radar, wherein the processor is configured to:

detect a first heartbeat signal of a driver through the radar;

extract a beat-to-beat interval signal from the first heartbeat signal;

generate heart rate variability data according to the beat-to-beat interval signal, wherein the heart rate variability data comprises low frequency power and high frequency power;

determine whether the driver is fatigued according to the heart rate variability data; and in response to determining that the driver is fatigued, output an alarm message, wherein the processor is configured to further:

obtain a historical data set, wherein the historical data set comprises historical heart rate variability data, wherein the historical heart rate variability data comprises historical low frequency power and historical high frequency power;

calculate a P-value of the heart rate variability data according to the historical data set and the heart rate variability data; and determine whether the driver is fatigued according to the P-value.

2. The driver monitoring system according to claim 1, wherein the processor is configured to further:

in response to the P-value being less than a threshold, determine that the driver is fatigued.

3. The driver monitoring system according to claim 1, wherein the processor calculates the P-value according to one of the following: analysis of variance, T-test, or F-test.

4. The driver monitoring system according to claim 1, wherein the processor is configured to further:

add the heart rate variability data to the historical data set to update the historical data set.

5. The driver monitoring system according to claim 4, wherein the processor is configured to further:

detect the first heartbeat signal and a second heartbeat signal of the driver according to a preset period, wherein the second heartbeat signal is later than the first heartbeat signal; and determine whether the driver is fatigued according to the updated historical data set and the second heartbeat signal.

6. The driver monitoring system according to claim 1, wherein the heart rate variability data further comprises a standard deviation of the beat-to-beat interval signal and a ratio of the low frequency power to the high frequency power.

7. The driver monitoring system according to claim 1, wherein the beat-to-beat interval signal comprises a first beat-to-beat interval, and wherein the processor is configured to further:

detect a first wave peak and a second wave peak of the first heartbeat signal, wherein the first wave peak and the second wave peak are adjacent R wave peaks; and calculate a time interval between the first wave peak and the second wave peak to obtain the first beat-to-beat interval.

8. The driver monitoring system according to claim 1, wherein the processor is configured to further:

perform a discrete Fourier transform on the beat-to-beat interval signal to obtain a frequency response; and obtain the low frequency power and the high frequency power from the frequency response.

9. The driver monitoring system according to claim 1, wherein the processor is configured to further:

detect an area within a vehicle through the radar to determine whether the driver exists; and in response to determining that the driver exists, detect the first heartbeat signal of the driver through the radar.

10. A driver monitoring method, comprising:

detecting a first heartbeat signal of a driver through a radar;

extracting a beat-to-beat interval signal from the first heartbeat signal;

generating heart rate variability data according to the beat-to-beat interval signal, wherein the heart rate variability data comprises low frequency power and high frequency power;

determining whether the driver is fatigued according to the heart rate variability data; and in response to determining that the driver is fatigued, outputting an alarm message, wherein determining whether the driver is fatigued according to the heart rate variability data comprises:

obtaining a historical data set, wherein the historical data set comprises historical heart rate variability data, wherein the historical heart rate variability data comprises historical low frequency power and historical high frequency power;

calculating a P-value of the heart rate variability data according to the historical data set and the heart rate variability data; and determining whether the driver is fatigued according to the P-value.

11. The driver monitoring method according to claim 10, wherein determining whether the driver is fatigued according to the P-value comprises:

in response to the P-value being less than a threshold, determining that the driver is fatigued.

12. The driver monitoring method according to claim 10, further comprising calculating the P-value according to one of the following: analysis of variance, T test, or F test.

13. The driver monitoring method according to claim 10, further comprising:

adding the heart rate variability data to the historical data set to update the historical data set.

14. The driver monitoring method according to claim 13, further comprising:

detecting the first heartbeat signal and a second heartbeat signal of the driver according to a preset period, wherein the second heartbeat signal is later than the first heartbeat signal; and determining whether the driver is fatigued according to the updated historical data set and the second heartbeat signal.

15. The driver monitoring method according to claim 10, wherein the heart rate variability data further comprises a standard deviation of the beat-to-beat interval signal and a ratio of the low frequency power to the high frequency power.

16. The driver monitoring method according to claim 10, wherein the beat-to-beat interval signal comprises a first beat-to-beat interval, wherein extracting the beat-to-beat interval signal from the first heartbeat signal comprises:

detecting a first wave peak and a second wave peak of the first heartbeat signal, wherein the first wave peak and the second wave peak are adjacent R wave peaks; and calculating a time interval between the first wave peak and the second wave peak to obtain the first beat-to-beat interval.

17. The driver monitoring method according to claim 10, wherein generating the heart rate variability data according to the beat-to-beat interval signal comprises:

performing a discrete Fourier transform on the beat-to-beat interval signal to obtain a frequency response; and obtaining the low frequency power and the high frequency power from the frequency response.

18. The driver monitoring method according to claim 10, further comprising:

detect an area within a vehicle through the radar to determine whether the driver exists; and in response to determining that the driver exists, detecting the first heartbeat signal of the driver through the radar.

* * * * *